ns* cited by examiner

(12) United States Patent
Chang et al.

(10) Patent No.: US 10,792,411 B2
(45) Date of Patent: Oct. 6, 2020

(54) ACCELERATED METHOD FOR PREPARING PLATELET RICH PLASMA

(71) Applicants: Jae-Hyung Robert Chang, Denver, CO (US); Giuseppe Intini, Wexford, PA (US)

(72) Inventors: Jae-Hyung Robert Chang, Denver, CO (US); Giuseppe Intini, Wexford, PA (US)

( * ) Notice: Subject to any disclaimer, the term of this patent is extended or adjusted under 35 U.S.C. 154(b) by 0 days.

(21) Appl. No.: 16/099,621

(22) PCT Filed: May 9, 2017

(86) PCT No.: PCT/US2017/031680
§ 371 (c)(1),
(2) Date: Nov. 7, 2018

(87) PCT Pub. No.: WO2017/196798
PCT Pub. Date: Nov. 16, 2017

(65) Prior Publication Data
US 2019/0134293 A1     May 9, 2019

Related U.S. Application Data

(60) Provisional application No. 62/333,536, filed on May 9, 2016.

(51) Int. Cl.
| | | |
|---|---|---|
| *A61M 1/36* | (2006.01) | |
| *B01D 21/00* | (2006.01) | |
| *A61M 1/02* | (2006.01) | |
| *B03C 1/01* | (2006.01) | |

(52) U.S. Cl.
CPC .......... *A61M 1/3618* (2014.02); *A61M 1/029* (2013.01); *A61M 1/0281* (2013.01); *B01D 21/00* (2013.01); *B01D 21/0009* (2013.01); *A61M 2202/0427* (2013.01); *B03C 1/01* (2013.01); *B03C 2201/18* (2013.01); *B03C 2201/26* (2013.01)

(58) Field of Classification Search
CPC .. A61M 1/3618; A61M 1/0281; A61M 1/029; B01D 21/00
See application file for complete search history.

(56) References Cited

U.S. PATENT DOCUMENTS

| | | |
|---|---|---|
| 4,765,899 A | 8/1988 | Wells et al. |
| 2009/0032449 A1* | 2/2009 | Mueth .................. G02B 21/32 210/94 |
| 2011/0042296 A1 | 2/2011 | Dorian et al. |
| 2015/0306212 A1 | 10/2015 | Kahvejian et al. |
| 2015/0328260 A1 | 11/2015 | Chow |

OTHER PUBLICATIONS

Plouffe et al., "Fundamentals and Application of Magnetic Particles in Cell Isolation and Enrichment", Rep Prog Phys Jan. 2015, 78(1) (Year: 2015).*

* cited by examiner

*Primary Examiner* — Ruth A Davis
(74) *Attorney, Agent, or Firm* — Hodgson Russ LLP

(57) ABSTRACT

Provided is an accelerated method for preparing platelet rich plasma (PrP) without centrifugation or filtration. The method comprises contacting a sample of whole blood with an anti-coagulant and an inducer of Rouleaux formation; allowing the mixture to stand thereby depleting the sample of RBCs, and collecting the platelet-rich plasma fraction. The PrP volume obtained by the present method is about 10-60% of the volume of the starting whole blood sample, and contains less than 200,000 RBCs and at least 100,000 platelets per microliter.

5 Claims, No Drawings

ACCELERATED METHOD FOR PREPARING PLATELET RICH PLASMA

CROSS-REFERENCE TO RELATED APPLICATIONS

This application claims priority to U.S. Provisional patent application No. 62/333,536, filed on May 9, 2016, the disclosure of which is incorporated herein by reference.

BACKGROUND OF THE DISCLOSURE

Platelets are important component of blood and bone marrow and are involved in various functions including wound healing, among others. These 200-2000 nm vesicle-like structures serve as a reservoir for growth factors and chemotactic factors important for wound healing and likely include exosomes from a clinical standpoint. While red blood cells (RBCs) play a vital role in the body, necrotic RBCs are capable of inducing tissue damage and overt, localized inflammation. Additionally, as the bone marrow is highly vascular and as the marrow produces much of the blood products (for example, RBC, white blood cells (WBCs), platelets), bone marrow aspirates are enriched with blood and its contents. Removing RBCs from blood or bone marrow aspirates to enrich regenerative properties of blood or bone marrow aspirate would be desirable. For example, while the blood contains many factors that would enhance wound healing/regenerative properties (such as growth factors, cytokines, and chemokines, among others that are stored in cells or extracellular vesicles, e.g., platelets and exosomes), RBC lysates are known to induce or prolong inflammation and cause damage to cells/tissues. As such, separating RBC from the rest of the components of blood would help harness the regenerative properties of one or more of the remaining components (such as, for example, platelets) found in blood.

Traditional method for platelet rich plasma (PrP) preparation involves bench-top centrifugation for processing small blood volume (≤100 ml) or apheresis for large blood volumes (>100 ml). Centrifuge-method for PrP preparation involves two-step centrifugation. The first, low centrifugation step allows separation of platelets and plasma from the RBCs using low speed centrifugation. A higher speed second step centrifugation allows for separating the platelets from the plasma. When the platelets are extracted from the plasma, the remaining plasma is referred to as platelet-poor plasma or PPP. Resuspension of the platelets in small volumes of plasma (smaller than the volume of the originally separated plasma) produces platelet-rich plasma or PrP. Several devices are currently available for PrP preparation with the common denominator being their dependence on centrifugation.

Though centrifuge is readily available in laboratory setting, its presence in a clinically setting is limiting or, if present, space consuming. Additionally, the centrifuge-method is technique/operator sensitive and, especially in clinical settings, may cause variations in terms of the quality of PrP. Finally, due to the technical limitation of a centrifuge, PrP preparation cannot be performed outside a clinical setting (i.e., rural undeveloped areas). As such, a centrifuge-free method and device for PrP preparation would be highly desirable.

SUMMARY OF THE DISCLOSURE

The present disclosure provides accelerated methods for preparing PrP without the use of a centrifuge or a filter. The method comprises obtaining a biological sample from which PrP is to be prepared, such as a sample of whole blood; contacting the sample with an anti-coagulant and an inducer of Rouleaux formation; allowing the sample to stand thereby depleting the sample of RBCs without subjecting the sample to centrifugation or filtration, and collecting the platelet-rich plasma fraction. The inducer of Rouleaux formation can be a polymer or a biological molecule that cause aggregation or stacking of RBCs.

In one embodiment, the inducer of Rouleaux formation can be conjugated to solid-phase immobilization materials, such as beads or columns. The bead may be a magnetic bead and in that case, a magnetic field can be applied during the step of depletion of RBCs. However, again, no centrifugation step is needed.

The PrP volume obtained by the present method is about 10-60% of the volume of the starting whole blood sample, and contains less than 200,000 RBCs and at least 100,000 platelets per microliter. For example, the PrP may contain less than 100,000 RBCs, and at least 150,000 platelets per microliter of PrP.

DESCRIPTION OF THE DISCLOSURE

This disclosure provides an accelerated Rouleaux formation/RBC aggregation based method for the rapid preparation of PrP. Data is provided to show that in the presence of an anti-coagulant such as acid citrate dextrose (ACD), hetastarch (hydroxylethyl starch) or any other starch, polymer, or substance with the same Rouleaux-forming/RBC aggregation properties as hetastarch, can be used to effectively separate erythrocytes out of blood without the need of centrifugation. By doing so, the platelet concentration within the remaining plasma (separated from the RBC) reaches levels comparable to or better than those observed in PrP traditionally prepared by centrifugation. The present method is time dependent (in that platelet concentration starts to decrease at longer incubation times).

We further observed that incorporation of high-density material into the RBC-hetastarch aggregate complex accelerates aggregate sedimentation. While not intending to be bound by any particular theory, it is considered that since a single hetastarch molecule is capable of forming multiple interactions with other hetastarch molecules, coupling aggregants (for example, hetastarch) to high-density material (such as high density polymer or metallic beads) may enhance the gravitational separation of the complex from plasma and platelets. Additionally, we observed that charged/magnetic beads or microspheres (or other solid-phase forms) allow for rapidly pulling down the RBC-hetastarch-magnetic bead aggregate complex using a magnet instead of relying on gravity only. Immobilization of hetastarch on other surfaces or compounds such as separation columns packed with hydroxyethyl-conjugated polystyrene, silica, metal (e.g., europium) beads may also allow for the trapping of RBCs while allowing platelets to flow through. Other potential RBC aggregants include fibrinogen, dextran, cellulose or hemagglutinin (e.g., lectin) and these may also be conjugated to polymer beads in order to separate RBC from blood. In addition, polymer beads may be derived from cellulose, metacrylate, polyethylene, polypropylene, polyethylene terephthalate (PET), polymethyl methacrylate, agarose, polyethylene glycol, and other plastic starting materials as well as naturally occurring composition materials such as palm nut shell, apricot pit shell, and glass ($SiO_2$, for example) may also be used.

The present disclosure provides accelerated methods for preparing PrP without the use of a centrifuge or a filter. The method comprises, consists essentially of, or consists of obtaining a sample of whole blood, depleting the sample of RBCs without subjecting the sample to centrifugation or filtration, and collecting the platelet-rich plasma fraction. This is achieved by adding agents to the whole blood sample that induce Rouleaux formation or other forms of RBC aggregation that would enhance RBC sedimentation. Rouleaux formation or stacking of RBC, is a type of RBC aggregation that is most commonly associated with infections. Macromolecules, such as fibrinogen, are known to facilitate aggregation of RBCs and such aggregation causes a change in RBC sedimentation rate, thereby allowing them to be separated out from rest of the blood. Polymers that can cause RBC aggregation include dextran, carboxymethylcellulose, and hydroxyethyl starch (of various molecular weight and hydroxyethylation levels), hydroxyethylated polymers (such as hydroxyethyl cellulose, polyhydroxyethylmethacrylate, polyhydroxyethyl urea), poly-L-lysine, among others.

In one aspect, the present method comprises obtaining a sample of blood or bone marrow aspirate from an individual, contacting the blood sample or bone marrow sample—simultaneously or sequentially—with an anti-coagulant and an inducer of Rouleaux formation, and after a suitable period of time, collecting the plasma, wherein the plasma is rich in platelets. The plasma may be substantially free of RBCs (for example, there may be less than 100,000 RBCs per microliter of the plasma). In the present method, the platelets are not concentrated out of blood and then resuspended in plasma. Rather, they are selectively enriched in the plasma without having to first remove them from the plasma.

The Rouleaux formation inducer can be used in a free form or can be conjugated to solid-phase immobilization materials (such as polymer beads, magnetic beads, plastic beads, cellulose, etc.), or both. In one embodiment, a portion of the Rouleaux formation inducer is present as a free agent and another portion is conjugated to beads to facilitate removal of RBCs. The beads may be magnetic beads and in such case, a magnetic field can be applied during incubation of the blood sample with the Rouleaux formation inducer to further accelerate RBC separation.

While specific reference may be made to whole blood herein, the description is equally applicable to bone marrow samples or other samples containing platelets.

A blood sample may be collected in any routine manner. For example blood may be conveniently drawn from a vein of an individual (such as the external jugular vein, antecubital veins, existing central lines, the wrist area, to name a few). The drawn blood may be directly collected in the container (generally referred to herein as a "tube") in which it is to be processed or may be collected in any standard collection tube and then transferred to the processing tube. The collected whole blood is exposed to an anti-coagulant as soon as collected. For example, the collection tube may pre-contain an amount of anti-coagulant sufficient to inhibit coagulation and/or an amount of Rouleaux formation inducer sufficient to induce RBC aggregation, or the anti-coagulant and/or Rouleaux formation agent may be added quickly into the collection tube after blood has been added to it or collected in it.

Similarly, bone marrow aspirate can be drawn and red blood cells can be separated as described above. Bone marrow aspirates are usually drawn from the pelvic bone or the sternum (breast bone). However other sources or routes are also considered. For instance, bone marrow aspirate can be obtained from mandibular and maxillary bone marrow cavities using an intraoral route of access.

In one embodiment, the walls of the processing container are nonadhesive or can be treated to be made nonadhesive. By "nonadhesive" is meant that it is not conducive for cell/platelet to adhere. The walls can be modified (for example, by fluorination) to render the surface not conducive for cell/platelet adherence. See "Introduction to Biomaterials" (Editor: Jeffrey O. Hollinger, CRC Press, Nov. 28, 2011; Chapter 5: Cell-Material Interactions: Fundamental Design Issues for Tissue Engineering and Clinical Considerations, p57) Examples of nonadhesive surfaces include bacteriological polystyrene, polypropylene, Teflons, fluorinated ethylene propylene, polytetrafluoroethylene, polyethylene, poly(propylene fumarate), polyvinylchloride, polylactides, and glass, among others.

The blood sample with the anti-coagulant and RBC Rouleaux formation inducer can be allowed to stand at room temperature (20-25° C.) or higher (such as from 25-37° C.) for a suitable period of time to achieve separation of RBCs. For example, the sample can be allowed to stand for up to 120 minutes (such as from 1 to 120 minutes and all values therebetween). However, it is preferable to allow the samples to stand for less than 60 minutes. For example, the samples can stand for 55, 45, 30, 25, 20, 15, 10 or 5 minutes. It was observed that the platelet concentration in the sample was optimal at from 10 to 30 minutes. Thus, in one embodiment, the sample is allowed to stand for 10-30 minutes and all values and ranges therebetween. After this, plasma can be collected. If the Rouleaux formation inducer is conjugated to a magnetic solid phase immobilization material, a magnetic field may be applied to further reduce the time of preparation. In one embodiment, the samples can be mixed with the anti-coagulant and the RBC Rouleaux formation inducer, where at least a portion of the Rouleaux formation inducer is attached to a magnetic material, and a magnetic field can be applied without waiting.

By the method of the present disclosure, at least 450 µl volume of platelet rich plasma/4.5 ml whole blood processed was obtained. Thus this disclosure provides a method where 10 to 60% of the whole blood volume can be recovered as a PrP fraction.

While any Rouleaux inducer can be used, one example of an inducer is hetastarch. It was observed that the ratio of hetastarch to whole blood-ACD was important. The ratio of hetastarch to whole blood can be in the range of 0.5-1.5% (v/v) hetastarch in whole blood-ACD solution. This is based on using a 6% hetastarch solution. Any other concentration of hydroxyethyl starch can be used. For example, 20% pentastarch solution is available commercially. Other concentrations of hetastarch or pentastarch or any other hydroxyethyl starch can be prepared. Based on the disclosure provided herein, it is within the purview of one skilled in the art to determine the amount of other concentrations of hydroxyethyl starch solutions to be added based on the disclosed ratio of 0.5-1.5% (v/v) for 6% hetastarch solution to whole blood.

Microbeads, among many solid-phase immobilization platforms available, have been adapted for separating biologically relevant products (proteins, nucleic acids, starch, etc). Some examples include streptavidin conjugated sepharose beads for capturing biotinylated macromolecules, nickel-conjugated agarose beads for isolating histidine-tagged proteins, and protein A agarose beads for immunoprecipitation studies. Recent improvements and innovations in microbead chemistry have led to fluorescent and/or magnetic beads. Hetastarch can be conjugated to any of the above beads. These microbeads enhance the density of the RBC-hetastarch complex, thereby positively enhancing the sedimentation rate. As such, hetastarch-coupled beads are useful for expediting the separation of RBC from blood by gravity.

The beads can be magnetic. Magnetic microbeads generally consist of a core (made of various inert compounds such as polystyrene or silica) that is coated with magnetite. For biological applications, these magnetic microbeads can be further encapsulated with chemically functional organic material (for example, see U.S. Pat. No. 8,945,509). The beads can then be conjugated to various biologically relevant macromolecules. Such beads are commercially available. For example, hydroxyethyl starch conjugated magnetic beads can be obtained from micromod Partikeltechnologie GmbH, Germany (product code #: 10-00-801, this is a 6% w/v solution). The magnetic beads may be biodegradable, such as iron-dextran beads.

If magnetic beads are used (such as hetastarch conjugated magnetic beads) and a magnetic field is applied, then the separation can be achieved in 10 or less minutes. For example, separation can be achieved in 10, 9, 8, 7, 6, 5, 4, 3 or 2 minutes. The blood sample with the anti-coagulant and RBC Rouleaux formation inducer (as a combination of conjugated and unconjugated forms) can be allowed to stand at room temperature for from 2 to 10 minutes and then subjected to a magnetic field. In an embodiment, the sample can be allowed to stand for up to 5 minutes (such as from 1 to 5 minutes) and then subjected to a magnetic field. In one embodiment, it is subjected to magnetic field without requiring standing.

By the method of the present disclosure, we were able to obtain at least 450 µl volume of platelet rich plasma/4.5 ml whole blood processed. Thus this disclosure provides a method where 10 to 60% of the whole blood volume can be recovered as a PrP fraction. For example, the present method can result in obtaining PrP which is 10, 15, 20, 25, 30, 35, 40, 45, 50, 55, or 60% of the whole blood volume from which it is prepared.

Data is provided herein to demonstrate that hydroxyethyl-starch coupled magnetic beads enhance gravitational sedimentation of RBC-hetastarch-magnetic bead aggregate when compared to RBC-hetastarch aggregate complex with approximately 300-400% improvement in RBC sedimentation (as determined by time to separate). If the beads are magnetic, use of magnet further enhanced separation by additional 300-400%. In summary, we demonstrate an innovative method for RBC sedimentation that is able to prepare PrP rapidly and effectively. Some of the unique features of our method includes: 1) enhancing hydroxyethyl starch based erythrocyte separation by mixing bead-conjugated hydroxyethyl starch with unconjugated hydroxyethyl starch (where hydroxyethyl starch is an example of a macromolecule capable of causing erythrocyte aggregation/Rouleaux formation and beads can be any solid-phase particle or magnetized solid-phase particle); 2) enhancing sedimentation rate of RBC-hydroxyethyl-bead complex through increasing the density of the said complex with solid-phase materials (example beads), and 3) use of magnet to effectively accelerate separation of RBCs from platelets.

The PrP prepared by the present method can contain less than 200,000 RBCs per microliter. For example, in various embodiments, the PrP prepared by the present methods may be 10-60% of the volume of the whole blood from which it is prepared, and contains less than 250,000, less than 200, 000, less than 150,000, less than 125,000, less than 100,000, less than 75,000, or less than 50,000 RBCs per microliter of PrP.

The PrP prepared by the present method may contain at least 100,000 platelets per microliters. For example, in various embodiments, the PrP prepared by the present method may be 10-60% of the volume of the whole blood from which it is prepared, and contains at least 100,000, 150,000, 200,000, 250,000, 300,000, 350,000, 400,000, 450, 000, 500,000, 600,000, 700,000, 800,000, 900,000, 1,000, 000 or 2,000,000 platelets per microliter of PrP. For example, the platelets can be from 100,000 to 500,000, 150,000 to 500,000, 200,000 to 500,000, 150,000 to 450, 000, 200,000 to 450,000, 100,000 to 1,000,000, 150,000 to 1,000,000, 200,000 to 1,000,000 and all ranges between 100,000 to 1,000,000 per microliter of the PrP. In one embodiment, the platelets can be up to 2,000,000 per microliter of the PrP.

For example, the present PrP contains less than 200,000 RBCs and at least 150,000 platelets per microliter. In various embodiments, the PrP prepared by the present methods is from 10-60% of the volume of whole blood from which it is prepared and contains: i) less than 150,000, 125,000, 100, 000, 75,000, or 50,000 RBCs, and ii) at least 150,000, 200,000, 250,000, 300,000, 350,000, 400,000, 450,000 and 500,000 platelets per microliter of PrP.

The following are examples of some embodiments of the present disclosure.

A method for preparing platelet rich plasma comprising: exposing a sample of whole blood to an anti-coagulant and an inducer of Rouleaux formation; allowing the mixture to stand at room temperature for a period of time sufficient for red blood cells to settle to the bottom; removing the platelet rich plasma fraction from the top, wherein no centrifugation step is used for the preparation of the platelet rich plasma and wherein the plasma fraction is at least 10-60% of the volume of the sample of whole blood and contains at least 100,000 platelets and less than 100,000 red blood cells per microliter.

A method for preparing platelet rich plasma comprising: exposing a sample of whole blood to ACD and hetastarch; allowing the mixture to stand at room temperature for a period of time sufficient for red blood cells to settle to the bottom; removing the platelet rich plasma fraction from the top, wherein no centrifugation step is used for the preparation of the platelet rich plasma.

A method for preparing platelet rich plasma comprising: exposing a sample of whole blood to an anti-coagulant (such as ACD) and an inducer of Rouleaux formation (such as hetastarch); allowing the mixture to stand at room temperature for less than 30 minutes, such as from 15 to 20 mins, and without a centrifugation step, removing the platelet rich plasma fraction from the top.

A method for preparing platelet rich plasma comprising: exposing a sample of whole blood to ACD and hetastarch, wherein a 0.5 to 1.5% v/v of a 6% solution of hetastarch is added to whole blood; allowing the mixture to stand at room temperature for less than 30 minutes, such as from 15 to 20 mins, and without a centrifugation step, removing the platelet rich plasma fraction from the top.

A method for preparing platelet rich plasma comprising: exposing a sample of whole blood to an anti-coagulant (such as ACD) and an inducer of Rouleaux formation in a smooth walled tube having an inner diameter of more than 8 mm, for example, a smooth walled tube, optionally made of glass, having an inner diameter of at least 10 mm, or in a tube having an inner diameter of about 15 mm; allowing the mixture to stand at room temperature for a sufficient period of time, such as for less than 30 minutes, and without a centrifugation step, removing the platelet rich plasma fraction from the top.

A method for preparing platelet rich plasma comprising: exposing a sample of whole blood to an anti-coagulant (such as ACD) and an inducer of Rouleaux formation (such as hetastarch); allowing the mixture to stand at room temperature for less than 30 minutes, such as from 15 to 20 mins, and without a centrifugation step, removing the platelet rich plasma fraction from the top, wherein some or all of the inducer of Rouleaux formation is conjugated to a solid-phase immobilization material, such as a magnetic bead.

A method for preparing platelet rich plasma comprising: exposing a sample of whole blood to an anti-coagulant (such as ACD) and an inducer of Rouleaux formation (such as hetastarch) conjugated to magnetic beads; applying a magnetic field at room temperature (generally from 18 to 25° C.) for less than 10 mins or less than 5 mins, and without a centrifugation step, removing the platelet rich plasma fraction, that is, the top fraction.

A method for preparing platelet rich plasma comprising: exposing a sample of whole blood to an anti-coagulant and an inducer of Rouleaux formation, wherein a portion of the inducer of Rouleaux is conjugated to magnetic beads and another portion is present as unconjugated; subjecting the mixture to a magnetic field such that red blood cells to settle to the bottom; without using a centrifugation step, removing the plasma fraction from the top.

A PrP which contains less than 200,000, less than 150,000, less than 125,000, less than 100,000, less than 75,000, or less than 50,000 RBCs per microliter of PrP, and contains at least 150,000, 200,000, 250,000, 300,000, 350,000, 400,000, 450,000, 500,000, 600,000, 7,000,000, 800,000, 900,000, or 1,000,000 platelets per microliter of PrP.

A PrP which is prepared by a method of any of the embodiments of the present disclosure.

The PrP prepared by the present method can be used for therapeutic, diagnostic, cosmetic or other uses. For example, the PrP may be used for wound and tissue repair, cosmetic applications alone or together with other agents (such as collagen, retinol, etc), plasma preparation, and injection into ligaments, articular spaces, muscles, bone cavities, bone defects, or subcutaneously. The PrP fraction (top fraction) may be further processed for white blood cell isolation or exosome/microvesicle extraction. The platelets, exosome/microvesicles isolated away from the RBC could be used for diagnostic purposes. Further, the platelets, and/or cells, and/or exosome/microvesicles prepared by the method could be used in the manufacture of therapeutics, including cellular and biological agents.

The following examples are provided for illustrative purposes and are not intended to be restrictive.

Example 1

In this example, the ability of hetastarch to effectively separate platelets from erythrocytes into a small fraction of plasma was tested. We compared the concentration of platelets found in the plasma separated by means of hetastarch to the concentration of platelets found in PrP prepared by the traditional method (centrifuge-based method).

For use as a control, PrP preparation was made as follows: approximately 9 ml whole blood was collected in a blood collection tube (BD Vacutainer ACD tube, sku #364606, BD Diagnostics, Franklin Lakes, N.J.) that contained 1 ml acid-citrate-dextrose buffer solution A (ACD, commonly used anticoagulant) with final whole blood:ACD ratio of approximately 9:1. 10 ml of ACD solution A consisted of 0.073 g citric Acid, anhydrous, 0.220 g sodium citrate, dehydrate, and 0.245 g dextrose, monohydrate that was dissolved in water. The whole blood-ACD mix was centrifuged on a desktop centrifuge for 2½ minutes. Plasma (~4-5 ml top layer containing platelet and WBC) was collected with aspirating syringe. The plasma was centrifuged for 5 minutes in order to pellet platelets (and WBC). The supernatant was labeled as platelet poor plasms or PPP. Platelets (the pellet) were resuspended with 500 µl of the PPP, resulting in a platelet concentration of 213,000/mm³. Platelet poor plasma (PPP) had a concentration of 22,500/mm³ platelets.

Hetastarch-based preparation of PrP: to 5 ml of whole blood-ACD solution (prepared as above at approximately 9:1 v/v ratio of whole blood to ACD solution), 1 ml of hetastarch solution (HetaSep™, StemCell Technologies, product catalog #07806, 6% Hetastarch) was added. After 15 minutes at room temperature, plasma containing platelets (~3 ml) was collected by aspiration with a syringe. Platelets in a sample of the collected plasma were counted. Results indicated the plasma contained 244,000 platelets/mm³. Therefore, the concentration of platelets in the PrP using hetastarch was at least as much as the concentration of platelets in the PrP obtained by the traditional centrifuge-based method. Considering final volumes of platelet collected (500 µl with centrifuge method vs. 3 ml for hetastarch method), the hetastarch method provides superior yield of total platelets.

Example 2

In this example, we tested whether an anticoagulant such as ACD is required for the hetastarch-based method to work. Additionally, we tested whether time has any influence on the concentration of platelets of the PrP prepared by the hetastarch-based method.

Experiment Condition 1

No ACD was used. 1 ml of Hetastarch solution (6%) was added to 4.5 ml of blood in the absence of ACD to induce RBC separation. It became clear after 1 hr of incubation, blood coagulation set in thereby producing serum instead of plasma. This was further confirmed by virtual absence of platelet in the serum fraction. As coagulation can activate and deplete platelet, this confirms that the use of anticoagulant is necessary for separating RBC from blood by RBC aggregation, including Rouleaux formation.

Experiment Condition 2

1 ml of ACD was added to 9 ml of blood to make the Whole-blood-ACD mix. 1 ml of 6% Hetastarch solution was added to 5 ml of Whole-blood-ACD mix (same source as used for control). 50 µl of plasma was sampled from the top of the plasma layer with a p200 pipettor at varying intervals. Plasma was sampled from below the meniscus (but well above the interface between plasma and RBC layers).

Control: PrP was prepared using centrifugation from 5 ml of whole blood-ACD as described above. PrP yielded 275,000 platelets/mm³. Supernatant (Platelet-Poor Plasma or PPP) yielded 1550 platelets/mm³.

Results indicate that ACD is required for the hetastarch-based method. In the absence of ACD, we observed blood coagulation and serum formation.

In the presence of ACD, plasma was formed. Results are shown in the table below (TABLE 1). Visual inspection showed noticeable plasma fraction at 10 minutes, and this was more prominent at 15 minutes. Plasma fraction at 30 minutes was 3-4 times the volume of the fraction at 15 minutes. It will be appreciated that other inducers of RBC aggregation will have different dynamics in aggregation formation and sedimentation. Based on the disclosure herein, separation time using other aggregants can be optimized for each aggregant.

The above experiments demonstrate that hetastarch is able to concentrate platelets; platelets settle to the bottom of the plasma fraction as suggested by decreasing count when collected from top of the plasma fraction (10-90 minutes); pooling and mixing the plasma fraction at 120 minutes had similar platelet count as at 15 minute fraction; plasma fraction at 15-30 minutes seems ideal considering platelet concentration and the ease of extracting such fraction due to volume.

TABLE 1

| Time (in minutes) after adding 1 ml of 6% Hetastarch | Platelet/mm$^3$ |
| --- | --- |
| 10 | 195,500 |
| 15 | 246,000 |
| 20 | 223,000 |
| 30 | 206,000 |
| 90 | 186,500 |

*Total plasma fraction was aspirated at 120 minutes point while other time points reflect sampling from the top of the plasma layer.

Example 3

In this example, we tested whether the concentration of platelets in the PrP obtained by the hetastarch-based method varies as a function of the hetastarch volume.

Two vials of whole blood-ACD mix were pooled. Three vacutainer tubes were filled with 0.5, 1.0, and 1.5 ml of 6% Hetastarch solution. 5 ml of pooled whole blood-ACD was added to each tube containing Hetastarch. After 20 minutes, plasma fraction was collected from each vial. Results are in TABLE 2 below. When 1.5 ml of hetastarch was added to 5 ml of whole blood-ACD, erythrocytes sedimented more rapidly as evidenced by lack of plasma fraction volume at 20 minutes versus at 90 minutes.

Control—PrP was prepared by centrifugation described in Example 1 using 10 ml of whole blood-ACD mix.

The results indicate that the ratio of 1 ml of hetastarch/5 ml of whole-blood-ACD is ideal in terms of volume of collectable PrP and concentration of platelets. This is because after 20 minutes 0.5 ml of hetastarch yields a volume of PrP too small to be clinically useful and 1.5 ml of hetastarch yields larger volumes that reduce the concentration of platelets. For example, using 6% hetastarch, a ratio of 0.75 to 1.25 mls of hetastarch to 5 mls of whole blood/ACD can be used.

TABLE 2

| Volume of 6% Hetastarch added to 5 ml of blood-ACD mix | Total Plasma fraction (ml) collected after 20 minutes | Platelet concentration (platelet/mm3) |
| --- | --- | --- |
| 0.5 | 0.4 | 470,000 |
| 1.0 | 1.7 | 316,000 |
| 1.5 | 3.0 | 256,500 |
| Control (centrifuge) | | |
| PrP | 0.5 | 380,000* |
| Platelet poor plasma | 4.0 | 6,250 |

*Total in 10 ml of whole blood-ACD mix.

Example 4

In this example, we tested other agents known to induce Rouleaux formation to determine if these could be used for preparation of PrP by the present method. The following reagents known to induce Rouleaux formation were used: hemagglutinin, dextran sulfate, fibrinogen, hydroxypropylmethylcellulose, and carboxylmethylcellulose.

Control: PrP was prepared using Hetastarch as described in Example 2 above.

Hemagglutinin (lectin) (Sigma, L-8629) was diluted to 1 mg/ml. 50 µl of 1 mg/ml lectin was added to 5 ml of whole blood-ACD (prepared as described in Example 2 above).

100 mg/ml Dextran Sulfate (Sigma, D6001) was used at 1:5 (100 mg Dextran Sulfate:Whole Blood-ACD). Final volume was 1 ml of 100 mg/ml Dextran Sulfate with 5 ml of Whole Blood-ACD.

Fibrinogen (Sigma, F3879) was dissolved in phosphate buffer solution to yield a 2.5 mg/ml stock solution. 50 µl of 2.5 mg/ml fibrinogen solution was added to 5 ml of Whole Blood-ACD for PrP separation.

50 mg/ml hydroxypropyl methylcellulose was prepared by slowly adding measured powder into heated (90° C.) water (⅓ the final volume) with constant and vigorous stirring. Room temperature water was used to bring the final volume to 100% and stirred for additional 30 minutes.

20 mg/ml carboxymethylcellulose was prepared by adding small amounts of carboxymethylcellulose to water with gentle agitation between each addition.

4 ACD-tubes containing 1 ml of ACD were used to collect blood from a single donor. Upon blood collection, total volume of whole blood-ACD was about 10 ml. The whole blood-ACD from the 4 tubes was pooled and 5 ml was used for each condition. Platelet count was performed on the platelet fraction upon separation (TABLE 3).

TABLE 3

| Reagent | Platelet Count Platelet/mm$^3$ | Incubation Time | Separation Characteristics | Comments |
| --- | --- | --- | --- | --- |
| Hetastarch | 400,000 | 20 minutes | Good, clear upper platelet fraction | |
| Lectin | N/A | | No separation after 1 hour | |

TABLE 3-continued

| Reagent | Platelet Count Platelet/mm³ | Incubation Time | Separation Characteristics | Comments |
|---|---|---|---|---|
| Fibrinogen | 630,000 | 1 hour | Upper platelet fraction was smaller than seen with hetastarch | Separation was noticeable after 30 minutes and adequate for use after 1 hour |
| Dextran Sulfate | 130,000 | 1 hour | Upper platelet fraction was smaller than seen with hetastarch | Separation was noticeable after 30 minutes and adequate for use after 1 hour |
| Carboxymethyl cellulose | 80,000 | 20 minutes | Good, clear upper platelet fraction | Low platelet count suggests regent may also be binding platelet. After mixing Whole Blood-ACD, the solution was still highly viscous |
| Hydroxymethyl cellulose | 40,000 | 1 hour | Good separation, but lot of clumpy debris | After mixing with whole blood-ACD, the solution was still highly viscous |

Results indicate that in addition to hetastarch, other reagents known to induce RBC aggregation can also allow separation of platelets from erythrocytes. At the concentrations tested, hetastarch demonstrated superiority in RBC separation compared to others.

Example 5

This example provides data on the effect of collection tube characteristics on sedimentation of RBCs in the presence of hetastarch.

5 ml of whole blood-ACD (9:1) was added to 1 ml of 6% Hetastarch in SANTOPRENE™ tubes (a mixture of in situ cross linking of EPDM rubber and polypropylene) with an inner diameter of ~8 mm or in clear polypropylene tubes with smooth inner walls (VWR® High-Performance Centrifuge Tubes cat #89039-670) with an inner diameter of ~15 mm.

Results of this experiment indicate that tubes made of clear polypropylene with smooth inner walls and with a bigger diameter are more effective than Santoprene tubes with smaller diameter for separation of platelets.

Example 6

In this example, we compared glass tubes with an internal diameter of ~15 mm (BD Vacutainer glass tubes for blood collection) to polypropylene tubes with smooth inner walls with an internal diameter of ~15 mm (VWR® High-Performance Centrifuge Tubes cat #89039-670). Other experimental conditions were the same as in Example 5.

Results of this experiment indicate that PrP prepared by means of clear polypropylene with smooth inner walls present with a higher amount of erythrocytes contamination (TABLE 4). Additionally, clear polypropylene with smooth inner walls required five additional minutes to achieve the same level of platelet separation observed in glass (in terms of PrP volume as well as platelet concentration).

TABLE 4

| Type of Tube | Platelet Count Platelet/mm³ | Incubation Time | Separation Characteristics |
|---|---|---|---|
| Glass | 390,000 | 20 minutes | Good, clear separation with little or no erythrocytes in fraction |
| Clear polypropylene | 400,000 | 25 minutes | Higher number of erythrocytes in the platelet fraction at 20 minutes |

The data presented in these examples demonstrated that among plastics, smoother inner surfaces favor PrP preparation by reducing the time required for an effective platelet separation; different inner diameters may also influence the Rouleaux formation, with bigger diameters favoring platelet separation; for reducing the erythrocytes contamination and the required time for separation, glass tubes are preferred over plastic tubes for preparation of PrP (when the inner diameter is maintained constant) if more efficient and quicker preparation of PrP is required.

Example 7

In this example, we tested if hydroxyethyl conjugated to beads was able to accelerate RBC separation. Hydroxyethyl starch conjugated magnetic beads were purchased from Partikeltechnologic GmbH (micromod Partikeltechnologie GmbH, Germany—product code #: 10-00-801) (hereafter referred to as "beads"). The beads are 80 nm in diameter and are provided at $2.9 \times 10^{13}$ beads/ml suspended in water. The beads are unstable at pH<4.0. The beads were tested alone or as mixed with unconjugated hetastarch to mediate and accelerate RBC aggregation.

In order to test if hydroxyethyl starch-conjugated beads were able to accelerate RBC separation, blood was collected in 2 Vacutainer ACD tube as before. The two tubes were pooled from which the following groups were run in this study to examine the use of hydroxyethyl-starch conjugated beads in PrP preparation:

1. CONTROL (TRADITIONAL) PrP: PrP was prepared using the centrifuge method, as described above, from 5 ml of whole blood-ACD mix.
2. BEADS: to 2.5 ml of whole blood-ACD, 0.5 ml of undiluted beads were added.
3. HETASTARCH ONLY METHOD: 2.5 ml of whole blood-ACD mix as described above, was mixed with 0.5 ml of 6% hetastarch (5:1 ratio)
4. BEADS+HETASTARCH METHOD: serial dilution of beads:hetastarch were prepared (see solution preparation below) and subsequently mixed with whole blood-ACD in the constant ratio of 5:1 (as per the hetastarch only method).
5. BEADS+HETASTARCH+MAGNET: 1:16 beads:hetastarch solution was added to blood-ACD (5:1 blood-ACD:beads-hetastarch solution) and incubated in a magnet (EasySep Magnet (cat. #18000, Stem Cell Technologies, Inc).

Bead-based solution preparation:
1:1—500 µl Bead (stock suspension) to 500 µl Hetastarch
1:2—500 µl of the 1:1 Bead sample to 500 µl Hetastarch
1:4—500 µl of the 1:2 Bead sample to 500 µl Hetastarch
1:8—500 µl of the 1:4 Bead sample to 500 µl Hetastarch
1:16—500 µl of the 1:8 Bead sample to 500 µl Hetastarch
1:100—10 µl Bead (stock suspension) to 990 µl Hetastarch Where relevant, the various groups were allowed to stand (also referred to as "incubated") at room temperature for the indicated times. Plasma fraction was collected and platelet numbers were determined. Other characteristics were also noted as indicated below.

The results are tabulated below:

TABLE 5

| PrP separation groups | Incubation time | Platelet count Platelets/mm³ | COMMENTS |
|---|---|---|---|
| Traditional PrP | | 425,000 | |
| Hetastarch-only method | 20 min | 485,000 | |
| Beads alone | | | Too many beads, no separation observable |
| 1:1 (beads:hetastrach) | 15 min | | Too many beads, no separation observable |
| 1:2 (beads:hetastrach) | 15 min | 370,000 | |
| 1:4 (beads:hetastrach) | 15 min | 405,000 | |
| 1:8 (beads:hetastrach) | 15 min | 425,000 | |
| 1:16 (beads:hetastrach) | 10 min | 305,000* | |
| 1:16 (beads:hetastrach) with MAGNET | 4 min | 320,000* | |

*Blood was on the bench for more than 1 hr before using it

As shown in Table 5, at beads:hetastarch ratios of 1:2—1:8, we were able to get highly enriched PrP. Considering how well 1:8 beads:hetastarch worked in preparing PrP, we prepared a 1:16 beads:hetastarch that also showed good PrP yield, even though the blood-ACD sample had been sitting at room temperature for over 1 hour.

In addition, we performed additional study to see if the use of a magnet to pull down magnetic beads would considerably accelerate the separation process. We prepared blood-ACD-beads-hetastarch mix in a 1.5 ml Eppendorf Tube and incubated the tube in a magnet (EasySep Magnet (cat. #18000, Stem Cell Technologies, Inc). As shown in Table 5, the magnet significantly accelerated the separation time by about 250% when compared to gravitation separation at the same beads:hetastarch ratio (1:16).

Example 8

In this experiment we tested again the ability of magnetic beads-hydroxyethyl starch (micromod Partikeltechnologie GmbH, Germany—product code #: 10-00-801)(hereafter "BEADS") mixed with hetastarch (hereafter HETA) in different ratio to mediate and accelerate platelet aggregation when mixed with whole blood collected with ACD (anticoagulant) in the constant ratio of 5:1 (whole blood-ACD: hetastarch (with or without beads)). For each sample we also tested the ability of a magnet to accelerate the preparation of PrP. To this end, we placed 1.0 ml of whole blood-ACD mix into 1.5 ml eppendorf tubes. To the whole blood-ACD mix, 0.2 ml of hetastarch or hetastarch with beads were added. The tubes were placed into a magnet. The various groups evaluated are shown in the table below.

A—Control (Centrifuge Method): PrP was prepared from 5 ml of whole blood-ACD as described above.

B1—Hetastarch: PrP was prepared from 1.0 ml of whole blood-ACD by adding 0.2 ml 6% Hetastarch as described above. After mixing with hetastarch, the sample was allowed to separate for 15 minutes and PrP was collected by aspiration.

B2—Hetastarch: PrP was prepared as in B1 but the time for separation was 4 minutes.

B3—Hetastarch: PrP was prepared as in B2 and the tube was placed in a magnet for 4 minutes.

C1—Hetastarch with Beads (16:1): PrP was prepared from 0.8 ml of whole blood-ACD with hetastarch: beads solution (16:1 free hetastarch to beads). The sample was allowed to separate by gravity for 15 minutes prior to collecting the plasma.

C2—Hetastarch with Beads (16:1): PrP was prepared as for C1 but the time for separation by gravity was 4 minutes.

C3—Hetastarch with Beads (16:1): PrP was prepared as for C2 but in the presence of magnet.

C4—PBS with Beads (16:1): PrP was prepared as for C3 but PBS was used to dilute the beads for a final PBS:beads ratio of 16:1. The sample was allowed to separate by magnet for 4 minutes.

D1—Hetastarch with Beads (32:1): PrP was prepared from 0.8 ml of whole blood-ACD with hetastarch: beads solution (32:1 free hetastarch to beads). The sample was allowed to separate by gravity for 15 minutes prior to collecting the plasma.

D2—Hetastarch with Beads (32:1): PrP was prepared as for C1 but the time for separation by gravity was 4 minutes.

D3—Hetastarch with Beads (32:1): PrP was prepared as for C2 but in the presence of magnet.

D4—PBS with Beads (32:1): PrP was prepared as for C3 but PBS was used to dilute the beads for a final PBS:beads ratio of 32:1. The sample was allowed to separate by magnet for 4 minutes.

E1—Hetastarch with Beads (100:1): PrP was prepared from 0.8 ml of whole blood-ACD with hetastarch: beads solution (100:1 free hetastarch to beads). The sample was allowed to separate by gravity for 15 minutes prior to collecting the plasma.

E2—Hetastarch with Beads (100:1): PrP was prepared as for C1 but the time for separation by gravity was 4 minutes.

E3—Hetastarch with Beads (100:1): PrP was prepared as for C2 but in the presence of magnet.

Results:

TABLE 6

| ID | METHOD OF PREPARATION | OBSERVATIONS | RBCs in PrP | PLATELET FINAL CONC (Platelets/mm$^3$) |
|---|---|---|---|---|
| A | Traditional PrP | Prepared as per usual protocol | RBCs (++) | 160,000 |
| B1 | HETA 15 min no magnet | ~5 mm PrP band is visible | Few RBCs (+) | 170,000 |
| B2 | HETA 4 min no magnet | No appreciable separation | ND | ND |
| B3 | HETA 4 min with magnet | No appreciable separation | ND | ND |
| C1 | HETA:beads (16:1) 15 min no magnet | ~1-2 mm PrP band is visible | RBCs (+++) | 80,000 |
| C2 | HETA:beads (16:1) 4 min no magnet | No appreciable separation | ND | ND |
| C3 | HETA:beads (16:1) 4 min with magnet | ~4 mm PrP band is visible | Few RBCs (+) | 195,000 |
| C4 | PBS:beads (16:1) 4 min with magnet | No appreciable separation | ND | ND |
| D1 | HETA:beads (32:1) 15 min no magnet | ~3 mm PrP band is visible | RBCs (+++) | 65,000 |
| D2 | HETA:beads (32:1) 4 min no magnet | No appreciable separation | ND | ND |
| D3 | HETA:beads (32:1) 4 min with magnet | ~4 mm PrP band is visible | Few RBCs (+) | 265,000 |
| D4 | PBS:beads (32:1) 4 min magnet | No appreciable separation | ND | ND |
| E1 | HETA:beads (100:1) 15 min no magnet | ~5 mm PrP band is visible | Few RBCs (+) | 190,000 |
| E2 | HETA:beads (100:1) 4 min no magnet | No appreciable separation | ND | ND |
| E3 | HETA:beads (100:1) 4 min with magnet | ~2 mm PrP band is visible | Few RBCs (+) | 180,000 |

$^a$ND, not determined due to lack of RBC separation.
:"(+)" means low numbers of RBCs in final PRP preparation (RBC contamination),
"(++)" means moderate numbers of RBCs in the final PrP preparation, and
"(+++)" means high numbers of RBCs in the final PrP preparation. Thus, within this table,
"(+)" is the best separation and
"(+++)" indicates poor separation.

As shown above in Table 6, hetastarch alone worked after 15 min of incubation at RT (B1, 5 mm band separation out of a 1 ml of blood in 1.5 ml microfuge tube). It did not work after 4 min incubation (B2) or after 4 min incubation in a magnet (B3). Therefore a magnet does not influence platelet separation time/efficiency in the absence of beads.

After 15 min of incubation, samples with Hetastarch alone (B1) or with various concentration of beads (C1, D1, and E1) presented with a certain platelet separation. However, in this condition (no magnet used) the presence of beads seems to impair separation (separation band observed in B1 and E1 is better than the one observed in C1 and D1). It was noted that separation ratio is maintained after 25 min of incubation as well when separation bands of 9 mm in B1, 5 mm in C1, 7 mm in D1, and 9 mm in E1 were measured.

No separation is observed in all samples incubated at RT without a magnet for 4 minutes (B2, C2, D2, E2). When the magnet was used (for 4 minutes) in samples containing beads, we observed platelet separation with volumes similar in 16:1 and in 32:1 hetastarch:beads dilutions (4 mm separation in C3 and 4 mm separation in D3) and smaller volume in samples with 100:1 hetastarch:beads dilution. Thus, a certain amount of beads seems to be required for an efficient separation of platelets, as few beads (as in 100:1) cannot efficiently pool down RBCs. Thus, in one embodiment, a 50:1 hetastarch:beads ratio or less is used. For example, a ratio of 16:1 to 50:1 (and all ratios therebetween can be used). With the disclosure provided herein, one skilled in the art can determine the optimal ratio.

No separation is observed when the beads were diluted with PBS (C4 and D4) instead of unconjugated hetastarch. Therefore, both unconjugated hetastarch and hetastarch conjugated to magnetic beads is required for separation by magnetic force.

As shown above in the table, magnet incubation with beads increase purity of PrP, as lower contamination of RBCs is consistently observed in samples containing beads incubated for 4 minutes with the magnet (C3, D3, E3). Levels of RBCs contamination in C3, D3, and E3 is similar to the one observed with the used of hetastarch alone for 15 min (B1).

Presence of beads increases RBCs contamination when magnet is not used, as samples C1 and D1 exhibited high RBCs contamination after 15 min of incubation at RT. When beads are in very low concentration (100:1, E1) their "contamination effect" seems to be negligible.

When it comes to concentration of platelets in the obtained PRPs, the most effective Hetastarch:Beads ratio is the 32:1 (D3, 265,000 platelets/ul). This ratio is able to generate a PrP with a concentration of platelets ~60% higher than the one obtained with a traditional centrifuge-based method of separation (A1) or the one obtained with Hetastarch alone at RT for 15 minutes (B1).

Platelet concentration increases with lower amount of beads (D3 versus C3) but decreases again when amount of beads is too low (E3). Based on manufacturer's technical data, the beads are supplied at 2.9×10$^{13}$/ml. Therefore, the final bead concentration during separation is 3.0×10$^{11}$/ml (C3), $1.5\times10^{11}$/ml (D3), and $4.8\times10^{10}$/ml (E3). Yet, concentration of platelets in PRPs obtained in C3 (too many beads) and E3 (not enough beads) is still comparable to the concentrations measured in PrP obtained by a traditional centrifuge-based method (A1) or by Hetastarch alone at RT for 15 minutes (B1). Therefore, it appears having final bead concentration of $4.8\times10^{10}$ to $3.0\times10^{11}$/ml is sufficient for obtaining PrP that is comparable to the centrifuge method. Furthermore, a final bead concentration range of $1.2\times10^{11}$ to $2.4\times10^{11}$/ml appears to be optimal for PrP preparation using both unconjugated hetastarch with hetastarch conjugated to the beads.

Example 9

The following samples (n=2) were tested (samples were generated as described in Example 9):
1) PRP (traditional method)
2) Hetastarch for 15 minutes
3) Hetastarch+Beads (16:1) for 4 minutes with magnet
4) Hetastarch+Beads (32:1) for 4 minutes with magnet
5) Hetastarch+Beads (100:1) for 4 minutes with magnet In each samples RBCs were counted using a standard hemocytometer (dilution of 1:100). Counts are reported in the table below (Table 7 and Table 8). Initial hematocrit of the blood was 5.38 million RBC/μl.

TABLE 7

Concentration of RBC for each microliter (μl) or PRP

| | PRP (traditional method) | Hetastarch for 15 mins | Hetastarch + Beads (16:1) for 4 mins with magnet | Hetastarch + Beads (32:1) for 4 mins with magnet | Hetastarch + Beads (100:1) for 4 mins with magnet |
|---|---|---|---|---|---|
| RBC (sample 1)/μl | 220,000 | 60,000 | 115,000 | 75,000 | 2,165,000 |
| RBC (sample 2)/μl | 270,000 | 50,000 | 75,000 | 110,000 | 2,640,000 |
| AVERAGE | 245,000 | 55,000 | 95,000 | 92,500 | 2,402,500 |

TABLE 8

Percent of RBC excluded in the PrP preparation

| | PRP (traditional method) | Hetastarch for 15 mins | Hetastarch + Beads (16:1) for 4 mins with magnet | Hetastarch + Beads (32:1) for 4 mins with magnet | Hetastarch + Beads (100:1) for 4 mins with magnet |
|---|---|---|---|---|---|
| RBC (sample 1)/μl | 95.91% | 98.88% | 97.86% | 98.61% | 59.76% |
| RBC (sample 2)/μl | 94.98% | 99.07% | 98.61% | 97.96% | 50.93% |
| AVERAGE | 95.45% | 98.98% | 98.24% | 98.29% | 55.35% |

These data show that compared to the traditional method, RBC count is lower when PrP is prepared with Hetastarch—with the exception of the 100 to 1 ratio of hetastarch to beads.

While the present invention has been disclosed through specific embodiments, various modifications will be apparent to those skilled in the art and such modifications are intended to be within the scope of the disclosure.

What is claimed is:

1. A method for preparing platelet rich plasma comprising:
  a) exposing a sample of whole blood to an anti-coagulant and an inducer of Rouleaux formation, wherein the inducer of Rouleaux formation is a starch wherein a portion of the inducer of Rouleaux is conjugated to magnetic beads and another portion is present as unconjugated, wherein the ratio of the unconjugated starch to starch conjugated to magnetic beads is from 2:1 to 50:1;
  b) subjecting the mixture from a) to a magnetic field such that red blood cells to settle to the bottom;
  c) removing the plasma fraction from the top,
wherein no centrifugation step is used, and wherein the plasma fraction contains at least 100,000 platelets and less than 100,000 red blood cells per microliter.

2. The method of claim 1, wherein step b) is carried out for 10 minutes or less.

3. The method of claim 2, wherein step b) is carried out for 5 minutes or less.

4. The method of claim 1, further comprising the step of allowing the mixture from a) to stand at room temperature before or after step b), prior to step c.

5. The method of claim 1, wherein the starch is hetastarch.

* * * * *